United States Patent [19]

Mardin et al.

[11] Patent Number: 4,552,874
[45] Date of Patent: Nov. 12, 1985

[54] PYRAZOLOOXAZINES, PYRAZOLOTHIAZINES, AND PRYAZOLOQUINOLINES AND THEIR USE AS MEDICAMENTS

[75] Inventors: Mithat Mardin, Wuppertal; Rudolf Sundermann, Leverkusen; Friedrich Hoffmeister, Wuppertal; Wolf-Dieter Busse, Wuppertal; Harald Horstmann, Wuppertal; Siegfried Raddatz, Cologne, all of Fed. Rep. of Germany

[73] Assignee: Bayer Aktiengesellschaft, Leverkusen, Fed. Rep. of Germany

[21] Appl. No.: 462,864

[22] Filed: Feb. 1, 1983

[30] Foreign Application Priority Data

Feb. 6, 1982 [DE] Fed. Rep. of Germany ....... 3204126

[51] Int. Cl.⁴ .................. A61K 31/535; A61K 31/54; C07D 498/04; C07D 513/04
[52] U.S. Cl. .................................. 514/222; 514/225; 514/227; 514/228; 514/229; 514/231; 514/232; 514/233; 514/234; 514/236; 514/237; 514/239; 514/293; 544/14; 544/34; 544/74; 544/99; 544/101; 546/64; 546/65; 546/82; 546/83
[58] Field of Search ....................... 544/14, 34, 74, 99, 544/101; 546/64, 65, 82, 83; 424/246, 248.4, 248.5, 248.51, 248.52, 248.53, 248.54, 248.55, 248.56, 248.57, 248.58, 256, 258; 514/222, 225, 227, 228, 229, 231, 232, 234, 236, 237, 239, 293

[56] References Cited

PUBLICATIONS

Mazharuddin et al., Tet. Letters, No. 4 (1971), pp. 307–310.
Aki et al., Chemical Abstracts, vol. 77 (1972), 139934r.
Maki et al., Chemical Abstracts, vol 78 (1973), 136199q.
Maki et al., Chemical Abstracts, vol. 81 (1974), 3953w.
Okafor et al., Chemical Abstracts, vol. 88 (1978), 190619w.

Primary Examiner—Richard L. Raymond
Attorney, Agent, or Firm—Sprung, Horn, Kramer & Woods

[57] ABSTRACT

The invention relates to pyrazolooxazines, pyrazolothiazines and pyrazoloquinolines defined herein by Formula I. The invention also includes compositions containing said Formula I compounds and methods for the use of said compounds and compositions for their lipoxygenase-inhibiting properties. Also included in the invention are methods for the manufacture of said compounds of Formula I.

9 Claims, No Drawings

PYRAZOLOOXAZINES, PYRAZOLOTHIAZINES, AND PRYAZOLOQUINOLINES AND THEIR USE AS MEDICAMENTS

The present invention relates to pyrazolooxazines, pyrazolothiazines and pyrazoloquinolines, a process for their preparation, their use as medicaments, in particular their use as inhibitors of lipoxygenase, medicaments containing these compounds and their preparation.

It is known that the metabolites of arachidonic acid, leukotriene and slow reacting substance of anaphylaxis (SRS-A), formed by the lipoxygenase enzyme, are involved in the development of inflammatory and allergic processes, compare E. J. Goetzl, Immunology 40,709 (1980) and Medical Clinis of North America 65, 809 (1981); Samuelsson et. al., Trends in Pharmacol. Sci. May 1980, 227 and Blood, 58, 658 (1981); Borgeat et. al., J. Med. Chem. 24, 121 (1981) and Int. J. Immunopharmac. 2, 281–293, (1980); Austen and Lewis, Nature, 293, 103 (1981).

Known inhibitors of lipoxygenase, such as nordihydroguaiaretic acid, 3-amino-1-(3-trifluoromethylphenyl)pyrazoline, phenidone and 5,8,11,14-eicosatetraynoic acid, either also act as inhibitors of cyclooxygenase or only act at very high concentrations. Inhibition of the cyclooxygenase enzyme in the metabolism of arachidonic acid leads to a global inhibition of prostaglandin synthesis and to a stimulation of the lipoxygenase route, which causes gastrotoxicity or pro-inflammatory and asthmatic effects (compare Yen and Kreutner, Agents and Actions, 10, 274 (1980) and Blackwell and Flower, Prostaglandins 16, 417 (1978); and compare also Brune et al., J. Pharm. Pharmacol. 33, 127–128 (1981); Higgs et al., Eur. J. Pharmacol. 66, 81–86 (1980) and Piper et al., Prostaglandins 19, 371 (1980)). In addition, inhibitors of lipoxygenase which are already known, such as 3-amino-1-(m-trifluoromethylphenyl)-2-pyrazoline have toxic side effects on systemic administration (for example orally). Thus, there is a need for compounds acting orally, which do not have these undesired side effects.

Surprisingly, the pyrazolo derivatives according to the invention already inhibit lipoxygenase in a concentration at which there is little effect on the cyclooxygenase.

The compounds according to the invention surprisingly also stimulate the synthesis of prostacyclin in arterial vessels in vitro, possibly as a consequence of their lipoxygenase-inhibitory property. (Gryglewski et al. Prostaglandins 89, 685 (1976)). In respect of this effect, the compounds have greater activity than the inhibitor of lipoxygenase mentioned, 3-amino-1-(m-trifluoromethylphenyl)-2-pyrazoline. (Proc. of British Pharmacological Society 920 P (1981). The compounds according to the invention also stimulate prostacyclin synthesis in strips of rabbit aorta.

The compounds according to the invention also have an antiinflammatory effect in the model of carrageenan-induced oedema, when they are administered systemically, especially orally, and locally, especially cutaneously. They also have an antimetastatic effect.

The pyrazolo derivatives according to the invention, which inhibit lipoxygenase, can thus be used as medicaments for the treatment of inflammatory and allergic processes. In particular, they can find use as antiinflammatory, antirheumatic, antiatherosclerotic, antithrombotic, antiarthrotic, antiasthmatic, antiallergic, antimetastatic, antihypertensive and gastroprotective agents.

The pyrazolooxazines, pyrazolothiazines and pyrazoloquinolines according to the invention correspond to the formula I in its isomeric forms Ia and Ib

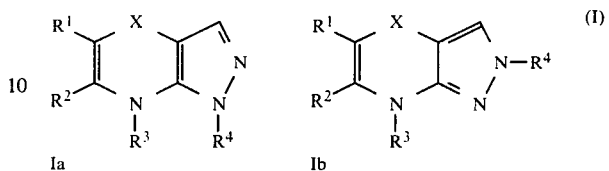

wherein

X denotes oxygen, sulphur, SO, $SO_2$ or methylene ($CH_2$), $R^1$ and $R^2$ represent a fused-on carbocyclic aryl or heteroaryl ring, which in turn can optionally be substituted by up to 5 identical or different substituents from the group comprising alkoxy, alkyl, aralkyl, cycloalkyl, aryl, alkylamino, dialkylamino, arylamino, aryloxy, arylthio, alkylthio, carboxyl, carboalkoxy, cyano, carbamoyl, sulphonyl, alkylsulphonyl, halogenoalkyl, halogenoalkoxy, halogen, amino, substituted amino, hydroxyl, sulphonamido, methylenecarboxyl, methylenecarboxyalkyl, propylenecarboxylalkyl or a dioxymethylene grouping, $R^3$ and $R^4$ can be identical or different and represent hydrogen, alkyl having 1 to 18 C atoms, it being possible for the alkyl radical to be interrupted once or several times by oxygen, sulphur or nitrogen; alkenyl or alkinyl having 2 to 12 (preferably 2 to 6) C atoms, aralkyl having 7 to 12 C atoms, it again being possible for the alkenyl, alkinyl and aralkyl radicals to be interrupted once or several times by oxygen, sulphur or nitrogen; aryl having 6 to 10 C atoms; heteroaryl; heteroaralkyl; alkylcarbonyl having 1 to 18 C atoms; heteroarylcarbonyl and arylcarbonyl having 7 to 11 C atoms, it being possible for these radicals optionally to be substituted by up to 5 identical or different substituents from the group comprising alkoxy, alkyl, aralkyl, cycloalkyl, aryl, alkylamino, dialkylamino, arylamino, aryloxy, arylthio, alkylthio, carboxyl, carboalkoxy, cyano, carbamoyl, sulphonyl, alkylsulphonyl, halogenoalkyl, halogenoalkoxy, halogen, amino- or substituted amino, hydroxyl, sulphonamido, methylenecarboxyl, methylenecarboxyalkyl or propylenecarboxyalkyl.

As used herein and unless otherwise specified, the terms "aryl" refers preferably to monocyclic or bicyclic carbocyclic aryl, such as phenyl, naphthyl or biphenyl; the term "heteroaryl" refers preferably to N-, O- or S-heterocyclics having 5 to 6 ring members, such as pyridyl, furyl and thienyl; the terms "alkyl", "alkoxy" and "alkylamino" preferably contain 1 to 18, especially 1 to 8 and more particularly 1 to 6 or 1 to 4 carbon atoms; the term "aralkyl" refers preferably to mono- or bi-cyclic carbocyclic aryl in the aromatic ring and 1 to 4, especially 1 to 2 carbon atoms in the alkyl portion, such as benzyl or phenethyl; the term "cycloalkyl" refers preferably to cycloalkyl having 4 to 8, especially 5 to 6 carbon atoms such as cyclopentyl or cyclohexyl; the term "dialkylamino" contains, in each alkyl group preferably 1 to 18, especially 1 to 8 and more particularly 1 to 6 or 1 to 4 carbon atoms; the term "carboalkoxy" preferably contains 1 to 4 carbon atoms in the alkoxy portion; the terms "halogenoalkyl" and "halogenoalkoxy" preferably contain 1 to 2 carbon atoms in the alkyl or alkoxy portions and are perhalogenated, especially in which the halogen atoms are chlorine or fluorine; the term "halogen" preferably denotes chlorine or fluorine; and "substituted amine as preferably amino which is mono- or di-substituted by $C_1$-$C_4$-alkyl or $C_1$-$C_4$-hydroxyalkyl.

When reference is made in the following text to the formula I, both isomeric forms, denoted Ia and Ib above, are always meant. Pyrazolooxazines, pyrazolothiazines and pyrazoloquinolines of the formula I are preferred, in which $R^1$ and $R^2$ represent a fused-on carbocyclic aryl or heteroaryl ring, which in turn can be substituted as stated above, $R^3$ and $R^4$ can be identical or different and represent hydrogen, alkyl having 1 to 18 C atoms, it being possible for the alkyl radical to be interrupted once or several times by oxygen, sulphur or nitrogen, aralkyl having 7 to 12 C atoms, heteroaralkyl, it being possible for the aralkyl and heteroaralkyl radicals to be interrupted once or several times by oxygen, sulphur and nitrogen, aryl having 6 to 10 C atoms and heteroaralkyl, and X has the abovementioned meaning.

Compounds of the general formula I according to the invention are particularly preferred, in which $R^1$ and $R^2$ represent a fused benzo or pyrido ring, which in turn can be substituted as stated above, $R^3$ and $R^4$ are not identical, it being possible for $R^3$ or $R^4$ to be hydrogen, whilst the other radical denotes alkyl having 1 to 18 C atoms, aralkyl having 7 to 12 C atoms or heteroaralkyl, it being possible for the alkyl, aralkyl and heteroaralkyl radicals to be interrupted once or several times by oxygen, sulphur and nitrogen, and X represents oxygen, sulphur or methylene.

Furthermore, the present invention comprises new compounds of the formula I, in this context again each of the two isomeric forms Ia and Ib being meant, and also their use in medicaments and for combating diseases, preferably inflammatory processes, especially as inhibitors of lipoxygenase and as substances stimulating the synthesis of prostacyclin and as vascular wall protectives and/or cytoprotectives, in particular as an antithrombotic, antimetastatic, antiatherosclerotic agent and/or ulcer prophylactic.

These new compounds are compounds of the formula I in its isomeric forms

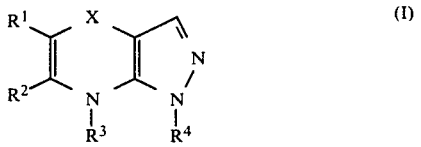
(I)

wherein

X denotes oxygen, sulphur, SO, $SO_2$ or methylene ($CH_2$), $R^1$ and $R^2$ represent a fused-on carbocyclic aryl or heteroaryl ring, which in turn can be optionally substituted by up to 5 identical or different substituents from the group comprising alkoxy, alkyl, aralkyl, cycloalkyl, aryl, alkylamino, dialkylamino, arylamino, aryloxy, arylthio, alkylthio, carboxyl, carboalkoxy, cyano, carbamoyl, sulphonyl, alkylsulphonyl, halogenoalkyl, halogenoalkoxy, halogen, amino, substituted amino, hydroxyl, sulphonamido, methylenecarboxyl, methylenecarboxyalkyl, propylenecarboxylalkyl or a dioxymethylene grouping, $R^3$ and $R^4$ can be identical or different and represent hydrogen, alkyl having 1 to 18 C atoms, it being possible for the alkyl radical to be interrupted once or several times by oxygen, sulphur or nitrogen, alkenyl or alkinyl having 1 to 12 C atoms, aralkyl having 7 to 12 C atoms, it again being possible for the alkenyl-alkinyl and aralkyl radicals to be interrupted once or several times by oxygen, sulphur or nitrogen, aryl having 6 to 10 C atoms, heteroaryl, heteroaralkyl, alkylcarbonyl having 1 to 18 C atoms, heteroarylcarbonyl and arylcarbonyl having 7 to 11 C atoms, it being possible for these radicals optionally to be substituted by up to 5 identical or different substituents from the group comprising alkoxy, alkyl, aralkyl, cycloalkyl, aryl, alkylamino, dialkylamino, arylamino, aryloxy, arylthio, alkylthio, carboxyl, carboalkoxy, cyano, carbamoyl, sulphonyl, alkylsulphonyl, halogenoalkyl, halogenoalkoxy, halogen, amino or substituted amino, hydroxyl, sulphonamido, methylenecarboxyl, methylenecarboxyalkyl or propylenecarboxyalkyl, but with the proviso that:

$R^1$ and $R^2$ together form a benzo ring and, when X is oxygen, $R^3$ denotes hydrogen and/or methyl and $R^4$ denotes hydrogen and/or methyl and, when X is sulphur, $R^3$ denotes hydrogen and $R^4$ denotes p-chlorophenyl or $R^3$ denotes acyl and $R^4$ denotes aryl.

The compounds of the formula I according to the invention can be prepared by reacting oxazinones, thiazinones and piperidinones of the formula II,

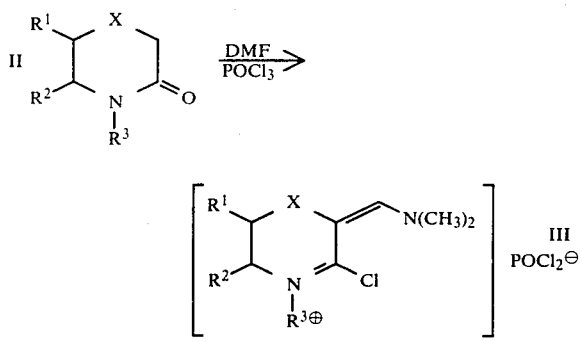

in which $R^1$, $R^2$, $R^3$ and X have the abovementioned meaning, with dimethylformamide and phosphorus oxychloride by the method of a Vilsmeier-Haack reaction (compare Mazharuddin and Thagarajan, Tetrahedron Letters 307, 1971), and reacting the salts of the general formula III thus produced with hydrazines of the general formula IV

wherein $R^5$ denotes hydrogen, alkyl having 1 to 18 C atoms, aralkyl having 7 to 12 C atoms, heteroaralkyl, it being possible for the alkyl, aralkyl and heteroaralkyl radicals to be interrupted once or several times by oxygen, sulphur and nitrogen, aryl having 6 to 10 C atoms and heteroaryl, it being possible for the aryl and heteroaryl radicals to be substituted by up to 5 identical or different substituents from the group comprising alkoxy, alkyl, aralkyl, cycloalkyl, aryl, alkylamino, dialkylamino, arylamino, aryloxy, arylthio, alkylthio, carboxyl, carboalkoxy, cyano, carbamoyl, sulphonyl, halogenoalkyl, halogenoalkoxy, halogen, amino or substituted amino, hydroxyl, sulphonamido, methylenecarboxyl, methylenecarboxyalkyl or propylenecarboxyalkyl.

The reaction of the salts of the formula III with the hydrazines of the formula IV is advantageously carried out in a polar solvent, for example in an alkanol, without a catalyst or in the presence of a base such as, for example, triethylamine, at a temperature between −80° C. and 100° C.

Preferably, the Vilsmeier-Haack salt of the formula III is reacted with the hydrazine of the general formula IV in ethanol at 80° C. in order to obtain a compound according to the invention (compare Aki and Nakagawa, Chem. Pharm. Bull. 20, 1325, 1972).

The compounds of the formula I according to the invention,
in which $R^3$ and $R^4$ represent alkylcarbonyl and/or arylcarbonyl with the abovementioned meaning,
can be prepared by reacting compounds of the formula I according to the invention,
in which $R^3$ and/or $R^4$ represent hydrogen,
with acylating agents, for example, acid (preferably carboxylic acid) halides or anhydrides of the formula V,
in which $R^5$ has the same meaning as $R^3$ and $R^4$, with the proviso that $R^5$ does not represent hydrogen.

(Y = imidazole, $OCOR^5$, Hal)
(Hal = Cl, Br, iodine)

The compounds of the formula II suitable for carrying out the invention are known or can be prepared by known methods. (In this context compare Shah et al, Indian Journal of Chemistry 7, 1006 (1969) and 10, 820 (1972)).

The hydrazines of the formula IV suitable for carrying out the invention are known or can be prepared by known methods.

Examples of compounds according to the invention are
pyrazolo[4,3-b][1,4]benzoxazine
7-methylpyrazolo[4,3-b][1,4]benzoxazine
7-chloropyrazolo[4,3-b][1,4]benzoxazine
5,7-dichloropyrazolo[4,3-b][1,4]benzoxazine
6-dimethylsulphonamidopyrazolo[4,3-b][1,4]benzoxazine
1-methylpyrazolo[4,3-b][1,4]benzoxazine
1-methyl-7-chloropyrazolo[4,3-b][1,4]benzoxazine
1-hydroxyethylpyrazolo[4,3-b][1,4]benzoxazine
1-phenylpyrazolo[4,3-b][1,4]benzoxazine
9-methylpyrazolo[4,3-b][1,4]benzoxazine
9-ethylpyrazolo[4,3-b][1,4]benzoxazine
pyrazolo[4,3-b][1,4]benzothiazine
7-chloro[4,3-b][1,4]benzothiazine
7-methyl[4,3-b][1,4]benzothiazine
1-phenyl-7-methylpyrazolo[4,3-b][1,4]benzothiazine
4-dioxopyrazolo[4,3-b][1,4]benzothiazine
pyrazolo[4,3-b][1,4]pyrido[3,2-b]oxazine
pyrazolo[4,3-b][1,4]naphthoxazine
1-methylpyrazolo[4,3-b][1,4]naphthoxazine
1-phenylpyrazolo[4,3-b][1,4]naphthoxazine Demonstration of the lipoxygenase-inhibitory properties of the compounds according to the invention is carried out in analogy to the method of Bailey et al., Journal of Biol. Chemistry 255, 5996, (1980) and of Blackwell and Flower, Prostaglandins 16, 417 (1978). In this test method, the metabolism of radioactively labelled arachidonic acid on washed human platelets is used. In this in vitro test, the radioactively labelled metabolites are extracted from the reaction mixture and separated by thin-layer chromatography. The autoradiogram is evaluated on a thin-layer scanner. Under these test conditions, the labelled metabolites are separated from the unreacted arachidonic acid and can then be evaluated quantitatively. The distribution of radioactivity over the products of cyclooxygenase formed during the metabolism, thromboxane $B_2$ ($TXB_2$) and 12-hydroxy-5,8,10-heptadecatrienoic acid (HHT) and the product of lipoxygenase, 12-hydroxy-5,8,11,14-eicosatetraenoic acid (HETE), under the influence of the inhibitors provides a measure of the inhibition of the enzymes.

The inhibition of lipoxygenase by the compounds according to the invention can be measured by the inhibition of synthesis of HETE. It emerges that the synthesis of $TXB_2$ and of HHT remains unaffected, whilst the conversion of arachidonic acid decreases. As can be seen from the following table, the compounds according to the invention bring about a significant inhibition of platelet lipoxygenase (HETE synthesis). (Compare Table 1).

The lipoxygenase inhibitory properties of the compounds according to the invention can also be demonstrated in leucocytes in analogy to the text above.

The polymorphonuclear leucocytes of humans and of rabbits metabolise arachidonic acid to 5-hydroxy-5,8,11,14-eicosatetraenoic acid (5-HETE) and leukotriene $B_4$ (5S, 12R-dihydroxy-6 cis, 8,10-trans-14 cis-eicosatetraenoic acid). The inhibition of the liberation of 5-HETE and leukotriene $B_4$ from the leucocytes provides a measure of the lipoxygenase-inhibitory effect of the compounds according to the invention. (Compare Table 1).

The test with human leucocytes is carried out by the method of Borgeat and Samuelsson (j. Biol. Chem. 254; 2643, 1979 and Proc. Natl. Acad. Sci. USA, 76, 2148 (1979), and with rabbit leucocytes by the method of Walker and Parish (Inter. Archs. Allergy appl. Immun. 66, 83, 1981).

The demonstration of the prostacyclin-stimulating effect is carried out by determining the liberation of prostacyclin after incubation of strips of rabbit aorta for one hour with the compounds according to the invention (analogous to the method of Moncada et al., Lancet 1977, I, 18) and subsequent radioimmunological determination of the stable prostacyclin metabolite 6-keto-PGF 1 (B. M. Peskar et al. FEBS Letters 121, 25, 1980) (compare Table 2).

The compounds according to the invention are also active in vivo. This activity is demonstrated by measuring the inhibition of Leucocyte migration by methods known per se (compare Higgs et al., Biochemical Pharmacology 28, 1959, (1979) and Eur. J. Pharmacol. 66, 81

(1981)). The compounds according to the invention also reduce the formation of oedema in the model of carrageenan inflammation, (compare Table 3) and inhibit the formation of metastases from B-16 melanoma (method of Honn, et. al. Science 212, 1270, 1981).

The new active compounds can be converted in a known manner into the customary formulations, such as tablets, capsules, coated tablets, pills, granules, aerosols, syrups, emulsions, suspensions and solutions, using inert, non-toxic pharmaceutically suitable vehicles or solvents. The therapeutically active compound should, in each case, be present in a concentration of about 0.5 to 90% by weight of the total mixture, that is to say in amounts which suffice to achieve the dosage range indicated.

The formulations are prepared, for example, by extending the active compounds with solvents and/or vehicles, optionally with the use of emulsifiers and/or dispersing agents, and, for example, when using water as the diluent, organic solvents can optionally be used as auxiliary solvents.

Examples of auxiliaries which may be mentioned are: Water, non-toxic organic solvents, such as paraffins (for example petroleum fractions), vegetable oils (for example groundnut oil/sesame oil), alcohols (for example ethyl alcohol and glycerol), glycols (for example propylene glycol and polyethylene glycol), N-alkylpyrrolidones, solid vehicles, such as, for example, natural rock powders (for example kaolins, aluminas, talc and chalk), synthetic rock powders (for example highly disperse silica and silicates) and sugar (for example cane sugar, lactose and glucose), emulsifiers, such as non-ionic anionic emulsifiers (for example polyoxyethylene fatty acid esters, polyoxyethylene fatty alcohol ethers, alkylsulphonates and arylsulphonates), dispersing agents (for example lignin, sulphite waste liquors, methylcellulose, starch and polyvinylpyrrolidone) and lubricants (for example magnesium stearate, talc, stearic acid and sodium lauryl sulphate).

Administration is effected in the customary manner, preferably orally or parenterally, in particular cutaneously and in the form of an aerosol. In the case of oral administration, the tablets can, of course, also contain, in addition to the vehicles mentioned, additives such as sodium citrate, calcium carbonate and dicalcium phosphate, together with various additional substances, such as starch, preferably potato starch, gelatine and the like. Furthermore, lubricants such as magnesium stearate, sodium lauryl sulphate and talc can also be used when making tablets. In the case of aqueous suspensions and/or elixirs which are intended for oral use, the active substances can be mixed with various flavour-improving agents or coloured or colouring materials in addition to the abovementioned auxiliaries.

In the case of parenteral administration, solutions of the active compounds employing suitable liquid vehicles can be used.

In general, it has proved advantageous, in the case of intravenous administration, to administer amounts of about 0.01 to 10 mg/kg, preferably about 0.05 to 5 mg/kg of body weight daily to achieve effective results, and in the case of oral administration, the dosage is about 0.05 to 100 mg/kg, preferably 0.1 to 10 mg/kg of body weight daily.

Nevertheless, it can at times be necessary to deviate from the amounts mentioned, and in particular to do so as a function of the body weight or of the nature of the administration route, but also because of the species and its individual behaviour towards the medicament, and the nature of the formulation of the medicament and the time or interval over which the administration takes place. Thus it can suffice in some cases to manage with less than the abovementioned minimum amount, whilst in other cases the upper limit mentioned must be exceeded. When relatively large amounts are administered, it can be advisable to divide these into several individual administrations over the course of the day. In this connection, the above statements similarly apply for administration both in human and also in veterinary medicine.

The following examples are intended to illustrate the invention in more detail: (see also Table 1).

EXAMPLE 1

(Compound No. 1 from Table 1)

14.9 g (0.1 mol) of benzoxazinone are dissolved in 50 ml of absolute DMF. 18.4 g (0.12 mol) of $POCl_3$ are added slowly dropwise at room temperature, during which the temperature rises to 80° C. After completion of reaction, a red salt crystallises out on cooling down, which is filtered off with suction and dissolved in alcohol. 12 g (0.24 mol) of hydrazine hydrate are slowly added dropwise to this solution. (Spontaneous heating, evolution of dimethylamine). After completion of reaction, the mixture is boiled under reflux for half an hour and then diluted with water. On cooling down, the product crystallises out.

Melting point 220° C., decomposition (from dilute alcohol)

Yield: 15 g (87%).

Preparation of the benzoxazinone (formula II, $R_1$ and $R_2$=benzo; $R_3$=H)

In a 1 liter conical flask, 109 g (1 mol) of o-aminophenol are dissolved in 500 ml of water and 85 ml of concentrated hydrochloric acid and are stirred with 15 g of active charcoal for 5 minutes. After filtering off the active charcoal with suction, the filtrate must be clear, and then the pH is adjusted carefully to 6-7 with sodium hydroxide solution. The product precipitated thereby is filtered off with suction and washed with water.

The o-aminophenol thus purified, which is still moist, is dissolved in 350 ml of water and 310 ml of acetone. 113 g (1 mol) of freshly distilled chloroacetyl chloride and, from a second dropping funnel, sodium hydroxide solution are simultaneously added dropwise to this solution, with stirring, so that a pH of 3 to 4 is maintained. After completion of reaction, the pH is adjusted to 7 with sodium hydroxide solution and the acetone is distilled off. The solution is now made strongly alkaline with concentrated sodium hydroxide solution at 70° C. and boiled under reflux for 10 minutes. After cooling down to 30° C., the pH is adjusted to 1 with concentrated hydrochloric acid and briefly boiled. After cooling down, the precipitated product is filtered off with suction, washed with water and dried.

Yield: 98 g, melting point 173° C.

EXAMPLE 2

(Compound No. 3, Table 1)

50 g (0.24 mol) of $PCl_5$ are slowly introduced into 300 ml of anhydrous dimethylformamide, with cooling in ice. A solution of 48 g (0.22 mol) of dichlorobenzomorpholone in 100 ml of dimethylformamide is now added rapidly at 20° C. During this, the temperature rises to about 50° C. The mixture is then stirred at 80° C. for a further 1 hour. After cooling down to room temperature, the red crystals are filtered off with suction and washed with a little dimethylformamide.

Melting point 202° C.

Yield: 46 g (64% of theory).

PCl5 is absolutely necessary in this reaction, since otherwise (for example with POCl3), the lactam group is not completely converted into the lactim chloride.

11.5 g of the salt prepared above are introduced into a solution of 15 ml of hydrazine hydrate in 70 ml of ethanol and the mixture is boiled under reflux. After completion of reaction, the precipitated pale yellow crystals are filtered off with suction and dried.

Melting point 230° C.

Yield: 6.4 g (76%)

EXAMPLE 3

(Compound No. 45, Table 1)

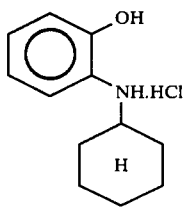

1. step

2-Cyclohexylaminophenol hydrochloride

A mixture of 10.9 g (0.1 mol) of 2-aminophenol and 10.4 g (0.1 mol) of cyclohexanone in 200 ml of ethanol is hydrogenated over 0.2 g of PtO2 under standard conditions, 0.1 mol of HCl in isopropanol is added to the reaction mixture, the catalyst is filtered off and the filtrate is evaporated in vacuo and the residue is precipitated with ether.

Yield: 16 g (70.3% of theory), melting point 258°-60° C.

2. step

4-Cyclohexylbenzo[1,4]oxazin-3-one

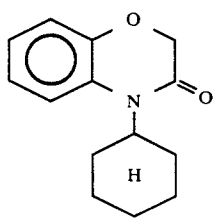

2.77 ml (20 mmols) of triethylamine and then 1.6 ml (20 mmols) of chloroacetyl chloride are added to a suspension of 4.55 g (20 mmols) of 2-cyclohexylaminophenol hydrochloride in 60 ml of absolute toluene and the mixture is heated under reflux for 1 hour. The suspension is shaked out with water, and after treatment with active charcoal, the organic phase is dried over Na2SO4 and distilled off. The remaining oil is taken up in 100 ml of ethanol and, after the addition of 3.1 g of potassium acetate, is heated under reflux for 1 hour. The residue remaining after evaporation of the solvent is chromatographed on silica gel with ethyl acetate/dichloromethane (1:4).

Yield: 2.1 g (69% of theory), oil.

3. step

9-Cyclohexylpyrazolo[4,3-b][1,4]benzoxazine

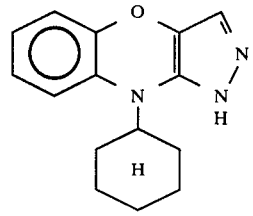

55 ml (0.598 mol) of POCl3 are added to a solution of 55 ml (0.716 mol) of DMF in 55 ml of ethylene chloride below 0° C. The suspension is warmed to room temperature, a solution of 53.6 g (0.232 mol) of 4-cyclohexylbenz[1,4]oxaxin-3-one is added, the mixture is boiled under reflux for 1 hour and the solvent is distilled off. The residue is taken up in 600 ml of ethanol, 83 ml (1.7 mols) of hydrazine hydrate are added below 30° and the mixture is stored overnight at room temperature. The solvent is evaporated, the residue is partitioned between water and dichloromethane, the organic phase is dried over Na2SO4, evaporated and the dry residue is chromatographed on silica gel with ethyl acetate/dichloromethane.

Yield 21.2 g (36% of theory) melting point 134°-35° C. (from ether/petroleum ether).

EXAMPLE 4

(Compound No. 39, Table 1)

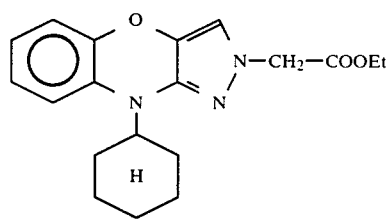

Ethyl (9-cyclohexylpyrazolo[4,3-b][1,4]benzoxazin-2-yl) acetate 0.96 g of sodium hydroxide (55-60% strength dispersion in oil) was added to a solution of 5.1 g (20 mmols) of 9-cyclohexylpyrazolo[4,3-b][1,4]benzoxazine in 50 ml of absolute THF, and after completion of evolution of hydrogen, 2.44 ml (22 mmols) of ethyl bromoacetate in 10 ml of absolute THF are added dropwise. After 2 hours, the solvent is distilled off, the residue is taken up in water and the solution is extracted with dichloromethane. The organic phase is dried, evaporated and the residue is chromatographed on silica gel with dichloromethane.

Yield 3.75 g (55% of theory), oil.

EXAMPLE 5

(Compound No. 40, Table 1)

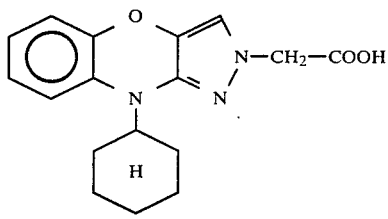

9-Cyclohexylpyrazolo[4,3-b][1,4]benzoxazine-2-acetic acid 3.6 g (10.6 mmols) of the ester described in the foregoing were dissolved in 20 ml of acetone, and 10 ml of water and 12 ml of N NaOH were added to the solution, the mixture was stirred for 30 minutes, diluted with water and extracted with dichloromethane. The aqueous phase is acidified and the precipitate produced is recrystallised from methanol/water.

Yield 2.75 g (83% of theory), melting point 113°–120° C.

EXAMPLE 6

(Compound No. 41, Table 1)

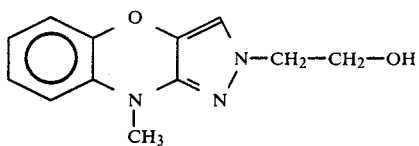

2-Hydroxyethyl-9-methylpyrazolo[4,3-b][1,4]benzoxazine

A mixture of 9.36 g (50 mmols) of 9-methyl-pyrazolo[4,3-b][1,4]benzoxazine and 13.2 g (150 mmols) of ethylene carbonate is stirred at 180°–200° C. for 10 minutes and at 200°–220° C. for 20 minutes and the mixture is separated by chromatography on silica gel with ethyl acetate.

Yield 5.5 g (47.4% of theory), melting point 87°–88° C.

EXAMPLE 7

(Compound No. 44, Table 1)

2-Acetyl-9-methylpyrazolo[4,3-b][1,4]benzoxazine

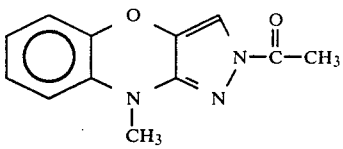

A solution of 7.5 g (40 mmols) of 9-methyl-pyrazolo[4,3-b][1,4]benzoxazine in 50 ml of absolute THF is added dropwise to a suspension of 1.8 g of sodium hydride (55–60% dispersion in oil) in 10 ml of absolute THF. After completion of evolution of hydrogen, 3.14 ml of acetyl chloride were added dropwise to the reaction mixture and the mixture was boiled under reflux for 3 hours. The solvent is removed in vacuo, the residue is taken up in water and the product is extracted at pH 7 with dichloromethane. The organic phase is evaporated and the residue is chromatographed on silica gel with ethyl acetate (dichloromethane (1:1)).

Yield 5.4 g (59% of theory), melting point 170°–71° C.

The compounds according to the invention from Table 1 were prepared in analogy to these examples.

TABLE 1

Examples

| No. | Compound | Melting point | Minimum concentration (g/ml) for inhibition of Lipoxygenase | |
|---|---|---|---|---|
| | | | in platelet | PMN Leucocytes |
| 1. | | 220° (decomposition) | $3 \cdot 10^{-7}$ | $3 \cdot 10^{-7}$ |
| 2. | | 230° C. (decomposition) | $10^{-6}$ | $10^{-6}$ |
| 3. | | 193° C. (decomposition) | $10^{-6}$ | $10^{-6}$ |

TABLE 1-continued

Examples

| No. | Compound | Melting point | Minimum concentration (g/ml) for inhibition of Lipoxygenase | |
|---|---|---|---|---|
| | | | in platelet | PMN Leucocytes |
| 4. | 3,5-dichloro-phenyl fused pyrazole (O, NH, NH) | 229° C. | $3 \cdot 10^{-7}$ | $10^{-6}$ |
| 5. | 4-SO$_2$NMe$_2$ phenyl fused pyrazole (O, NH, NH) | 262° C. | $10^{-5}$ | $5 \cdot 10^{-5}$ |
| 6. | phenyl fused pyrazole (O, NH, N-CH$_3$) | 172° C. | $10^{-6}$ | $10^{-6}$ |
| 7. | 4-Cl-phenyl fused pyrazole (O, NH, N-CH$_3$) | | $10^{-6}$ | $10^{-6}$ |
| 8. | phenyl fused pyrazole (O, NH, N-CH$_2$CH$_2$OH) | 145° C. | $5 \cdot 10^{-5}$ | $5 \cdot 10^{-5}$ |
| 9. | phenyl fused pyrazole (O, NH, N-phenyl) | 220° C. | $5 \cdot 10^{-5}$ | $5 \cdot 10^{-5}$ |
| 10. | phenyl fused pyrazole (O, N-CH$_3$, NH) | 167° C. | $3 \cdot 10^{-7}$ | $3 \cdot 10^{-7}$ |
| 11. | phenyl fused pyrazole (O, N-C$_2$H$_5$, NH) | 149-151° C. | $3 \cdot 10^{-7}$ | $3 \cdot 10^{-7}$ |
| 12. | phenyl fused pyrazole (S, NH, NH) | 178° C. | $3 \cdot 10^{-7}$ | $3 \cdot 10^{-7}$ |

TABLE 1-continued

Examples

| No. | Compound | Melting point | Minimum concentration (g/ml) for inhibition of Lipoxygenase | |
|---|---|---|---|---|
| | | | in platelet | PMN Leucocytes |
| 13. | (chloro-phenyl fused with S/NH to pyrazole NH) | 156° C. | $10^{-6}$ | $3 \cdot 10^{-7}$ |
| 14. | (methyl-phenyl fused with S/NH to pyrazole NH) | 174° C. | $10^{-6}$ | $10^{-6}$ |
| 15. | (methyl-phenyl fused with S/NH to N-phenyl pyrazole) | 198° C. | $10^5$ | $10^{-5}$ |
| 16. | (phenyl-SO$_2$/NH fused to pyrazole NH) | 268° C. | $>5 \cdot 10^{-5}$ | $>5 \cdot 10^{-5}$ |
| 17. | (pyridine fused via O/NH to pyrazole NH) | 231° C. | $5 \cdot 10^{-5}$ | $5 \cdot 10^{-5}$ |
| 18. | (naphthyl fused via O/NH to pyrazole NH) | >240 | $10^{-6}$ | $10^{-6}$ |
| 19. | (naphthyl fused via O/NH to N-methyl pyrazole) | 168° C. | $3 \cdot 10^{-6}$ | $3 \cdot 10^{-6}$ |
| 20. | (naphthyl fused via O/NH to N-phenyl pyrazole) | 181° C. | $>5 \cdot 10^{-5}$ | $>5 \cdot 10^{-5}$ |
| 21. | (quinoline-CH$_2$ fused to pyrazole NH/NH) | 165–169° C. | $>5 \cdot 10^{-5}$ | $>5 \cdot 10^{-5}$ |

TABLE 1-continued

| No. | Compound | Melting point | Minimum concentration (g/ml) for inhibition of Lipoxygenase | |
|---|---|---|---|---|
| | | | in platelet | PMN Leucocytes |
| 22. | [pyrazolo-quinoline with N-phenyl] | 164–167° C. | $>5 \cdot 10^{-5}$ | $>5 \cdot 10^{-5}$ |
| 23. | [pyrazolo-quinoline with N-CH$_3$] | 173° C. | $>5 \cdot 10^{-5}$ | $>5 \cdot 10^{-5}$ |
| 24. | [benzoxazine-pyrazole with two N-CH$_3$] | 102° C. | $>5 \cdot 10^{5}$ | $>5 \cdot 10^{5}$ |
| 25. | [compound with N-CH$_3$ groups] | 77–81 | not determined | $>10^{-5}$ |
| 26. | [compound with N-CH$_3$, N-phenyl × HCl] | 140–145 | not determined | $>10^{-5}$ |
| 27. | [compound with N-COCH$_3$, N-CH$_3$] | 156–158 | not determined | $>10^{-5}$ |
| 28. | [compound with N-CH$_3$, CO-phenyl-Cl] | 137–138 | not determined | $>10^{-5}$ |
| 29. | [compound with N-phenyl, NH] | 174 | not determined | $>10^{-5}$ |

TABLE 1-continued

Examples

| No. | Compound | Melting point | Minimum concentration (g/ml) for inhibition of Lipoxygenase | |
|-----|----------|---------------|-----------------------------------------------------------|--|
| | | | in platelet | PMN Leucocytes |
| 30. | | 120 | not determined | $10^{-5}$ |
| 31. | | 176 | not determined | $<10^{-6}$ |
| 32. | | 102 | not determined | $<10^{-6}$ |
| 33. | | 83 | not determined | $>10^{-5}$ |
| 34. | | 230 | not determined | $<10^{-6}$ |
| 35. | | 182–4 | not determined | $<10^{-6}$ |
| 36. | | 158 | not determined | $<10^{-6}$ |
| 37. | | 174–175 | not determined | $10^{-6}$ |
| 38. | | 102 | not determined | $10^{-6}$ |

TABLE 1-continued

Examples

| No. | Compound | Melting point | Minimum concentration (g/ml) for inhibition of Lipoxygenase in platelet | PMN Leucocytes |
|---|---|---|---|---|
| 39. | (benzoxazine fused pyrazole, N—CH₂CO₂Et, N-cyclohexyl) | Example 4 | not determined | $>10^{-5}$ |
| 40. | (benzoxazine fused pyrazole, N—CH₂COOH, N-CH₃) | Example 5 | not determined | $>10^{-5}$ |
| 41. | (benzoxazine fused pyrazole, N—CH₂CH₂OH, N-CH₃) | Example 6 | not determined | $>10^{-5}$ |
| 42. | (benzoxazine fused pyrazole, N—CO-pyridyl, N-CH₃) | 164–65° C. | not determined | $>10^{-5}$ |
| 43. | (benzoxazine fused pyrazole, NH, N—CH₂CO₂C₂H₅) | 127° C. | not determined | $>10^{-5}$ |
| 44. | (benzoxazine fused pyrazole, NCOCH₃, N-CH₃) | 170–71° C. | not determined | $>10^{-5}$ |
| 45. | (benzoxazine fused triazole, NH, N-cyclohexyl) | 134–135° C. | not determined | $10^{-6}$ |
| 46. | (benzothiazine fused pyrazole, NCOCH₃, N-CH₃) | 175–76° C. | not determined | $>10^{-5}$ |

TABLE 1-continued
Examples
| No. | Compound | Melting point | Minimum concentration (g/ml) for inhibition of Lipoxygenase in platelet | PMN Leucocytes |
|---|---|---|---|---|
| 47. | 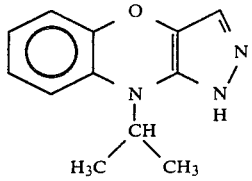 | 150–52° C. | not determined | $<10^{-6}$ |
| 48. | 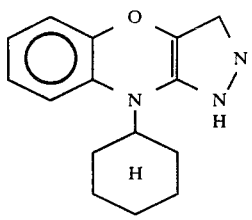 | 92–4° C. | not determined | $>10^{-6}$ |
| 49. | 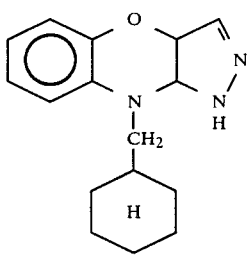 | 190° C. | not determined | $10^{-5}$ |
| 50. | 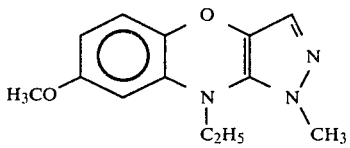 | 102° C. | not determined | $10^{-5}$ |
| 51. | 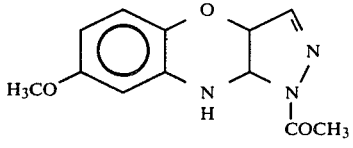 | 161° C. | not determined | $10^{-5}$ |
| 52. | 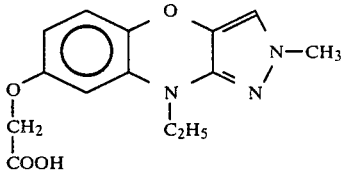 | 228° C. | not determined | $10^{-5}$ |
| 53. | 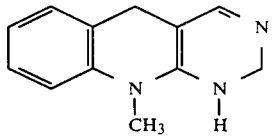 | 163–6° C. | | $>10$ |

TABLE 1-continued

Examples

| No. | Compound | Melting point | Minimum concentration (g/ml) for inhibition of Lipoxygenase | |
|---|---|---|---|---|
| | | | in platelet | PMN Leucocytes |
| 54. | | 91–2° C. | | $>10^{-5}$ |
| 55. | | 104° C. | | $>10^{-5}$ |
| 56. | | 130° C. | | $>10^{-5}$ |
| 57. | | 141–2° C. | | $>10^{-5}$ |
| 58. | | 159° C. | | $<10^{-5}$ |
| 59. | | Oil | | $10^{-5}$ |
| 60. | | Oil | | $>10^{-5}$ |

TABLE 1-continued

Examples

| No. | Compound | Melting point | Minimum concentration (g/ml) for inhibition of Lipoxygenase | |
|---|---|---|---|---|
| | | | in platelet | PMN Leucocytes |
| 61. | | 70–1° C. | | >10$^{-5}$ |
| 62. | | 93–5° C. | | >10$^{-5}$ |
| 63. | | 113–20° C. | | >10$^{-5}$ |
| 64. | | 128° C. | | >10$^{-5}$ |
| 65. | | 184–6° C. | | <10$^{-5}$ |
| 66. | | 151–5° C. | | <10$^{-5}$ |
| 67. | | 194–8° C. | | 10$^{-5}$ |

TABLE 1-continued

Examples

| No. | Compound | Melting point | Minimum concentration (g/ml) for inhibition of Lipoxygenase | |
|---|---|---|---|---|
| | | | in platelet | PMN Leucocytes |
| 68. | [structure: benzyl-O-phenyl fused oxazine-pyrimidine, N-CH3, N-H] | 178° C. | | $<10^{-5}$ |
| 69. | [structure: H3CO-phenyl fused oxazine-pyrimidine, N-CH3, N-H] | 159-60° C. | | $<10^{-5}$ |
| 70. | [structure: H3C—(CH2)3—O-phenyl fused oxazine-pyrimidine, N-CH3, N-H] | 145° C. | | $<10^{-5}$ |
| 71 | [structure: F3CS-phenyl fused oxazine-pyrimidine, N-CH3, N-H] | 152-55° C. | | $<10^{-5}$ |
| 72. | [structure: H3CO-phenyl fused oxazine-pyrimidine, N-CH3, N-CH3] | 126-8° C. | | $>10^{-5}$ |
| 73. | [structure: phenyl fused oxazine-pyrimidine, N-CH2CH2-O-CH2-phenyl, N-H] | 126-7° C. | | $10^{-5}$ |
| 74. | [structure: phenyl fused oxazine-pyrimidine, N-CH2CH2OH, N-H] | 175-8° C. | | $<10^{-5}$ |
| 75. | [structure: H3CO-phenyl fused oxazine-pyrimidine, N-CH2CH3, N-H] | 136° C. | | $<10^{-5}$ |

TABLE 1-continued

Examples

| No. | Compound | Melting point | Minimum concentration (g/ml) for inhibition of Lipoxygenase in platelet | PMN Leucocytes |
|---|---|---|---|---|
| 76. | (structure) | >270° C. | | <10⁻⁵ |
| 77. | (structure) | | | |
| 78. | (structure) | 192° C. | | |
| 79. | (structure) | | | |
| 80. | (structure) | | | |

TABLE 2

Stimulation of prostacyclin synthesis in strips of rabbit aorta at a concentration of 2.10⁶ g/ml of substance

| Compound | Stimulation in % compared to control |
|---|---|
| 12 | 80 |
| 17 | 200 |
| 24 | 100 (at 10⁻⁵ g/ml substance concentration) |

TABLE 3

Inhibition of carrageenan oedema formation after oral administration of 25 mg/kg to the rat

| Compound | % Inhibition |
|---|---|
| 2 | 57.8 |
| 3 | 41.4 |
| 9 | 75.1 |
| 10 | 73.4 |
| 16 | 45.4 |
| 27 | 62.4 |
| 36 | 60 |
| 39 | 47.5 |
| 40 | 44 |
| 42 | 67.3 |
| 44 | 70 |

TABLE 4

Inhibition of the initiation of pulmonary metastases in melanoma B 16 of the mouse after three i.p. administrations of 1 mg/kg (method of Honn, et al. Science 212, 1270, 1981).

| Compound | % Inhibition |
|---|---|
| 18 | 36% |
| 19 | 30% |

What is claimed is:

1. A compound of the formulae

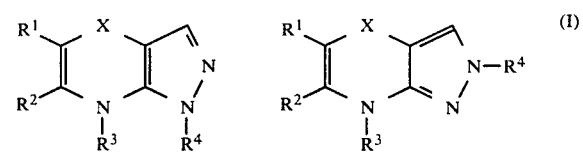

wherein $R^1$ and $R^2$ represent a fused-on carbocyclic aryl or a 5- or 6-membered N—, O— or S— fused-on heteroaryl ring, which in turn can optionally be substituted by up to 5 identical or different substituents from the group consisting of $C_1$-$C_{18}$-alkyl, -alkoxy or -alkylamino; mono- or bicyclic carbocyclic aralkyl having $C_1$–$C_4$-alkyl in the alkyl portion; $C_4$–$C_8$-cycloalkyl; dialkylamino having 1 to 18 carbon atoms in each alkyl group; carboalkoxy with $C_1$–$C_4$ in the alkoxy portion; halogenoalkyl, halogenalkoxy having 1 to 2 carbon atoms in the alkyl or alkoxy portion; X is O, S, SO, $SO_2$ or $CH_2$; $R^3$ and $R^4$ can be identical or different and represent hydrogen, alkyl having 1 to 18 C atoms, it being possible for the alkyl radical to be interrupted once or several times by oxygen, sulphur or nitrogen, alkenyl or alkinyl having 2 to 12 C atoms, aralkyl having 7 to 12 C atoms, it again being possible for the alkenyl, alkinyl and aralkyl radicals to be interrupted once or several times by oxygen, sulphur or nitrogen, aryl having 6 to 10 C atoms, heteroaryl, heteroaralkyl, alkylcarbonyl having 1 to 18 C atoms, heteroarylcarbonyl and arylcarbonyl having 7 to 11 C atoms, it being possible for these radicals optionally to be substituted by up to 5 identical or different substituents from the group comprising alkoxy, alkyl, aralkyl, cycloalkyl, aryl, alkylamino, dialkylamino, arylamino, aryloxy, arylthio, alkylthio, carboxyl, carboalkoxy, cyano, carbamoyl, alkylsulphonyl, halogenoalkyl, halogenoalkoxy, halogen, amino, hydroxyl, sulphonamido, methylenecarboxyl, methylenecarboxyalkyl or propylenecarboxyalkyl, but with the proviso that:

when X is oxygen, $R^3$ is other than hydrogen or alkyl and $R^4$ is other than hydrogen or alkyl and, when X is sulphur, $R^3$ is other than hydrogen and $R^4$ is other than p-chlorophenyl or $R^3$ is other than acyl and $R^4$ is other than aryl.

2. A compound of claim 1 wherein X is oxygen; $R^1$ is as defined in claim 1; $R^3$ is hydrogen; and $R^4$ is hydroxyethyl.

3. A compound of claim 1 wherein X is oxygen; $R^1$ is hydrogen; $R^3$ is benzyl and $R^4$ is hydrogen.

4. A pharmaceutical composition comprising a lipoxygenase-inhibiting amount of a compound of claim 1 together with an inert pharmaceutical carrier.

5. A pharmaceutical composition of claim 4 in the form of a sterile or physiologically isotonic aqueous solution.

6. A pharmaceutical composition of claim 4 in the form of a sterile or physiologically isotonic aqueous solution.

7. A composition of claim 4 in dosage unit form.

8. A composition of claim 7 in the form of tablets, pills, dragees, capsules, ampoules or suppositories.

9. A method of inhibiting lipoxygenase in a warm-blooded animal which comprises administering to said animal a lipoxygenase-inhibiting amount of a compound of claim 1 either alone, in admixture with an inert pharmaceutical carrier or in the form of a medicament.

* * * * *

UNITED STATES PATENT AND TRADEMARK OFFICE
CERTIFICATE OF CORRECTION

PATENT NO. : 4,552,874

DATED : November 12, 1985

INVENTOR(S) : Mithat Mardin, et al.

It is certified that error appears in the above-identified patent and that said Letters Patent is hereby corrected as shown below:

| | |
|---|---|
| Col. 2, line 57 | After "pyridyl" insert --morpholinyl-- |
| Col. 10, line 24 | Delete "oxaxin" and substitute --oxazin-- |
| Col. 24, Compound No. 53, last column | Delete "10" and substitute $--10^{-5}--$ |

Signed and Sealed this

Fifteenth Day of April 1986

[SEAL]

Attest:

Attesting Officer

DONALD J. QUIGG

Commissioner of Patents and Trademarks